United States Patent [19]
Chow et al.

[11] Patent Number: 5,091,642
[45] Date of Patent: Feb. 25, 1992

[54] COLORIMETRIC DETECTION APPARATUS

[75] Inventors: Vincent Chow, Hanover Park; Byron Denenberg, Northfield, both of Ill.

[73] Assignee: MDA Scientific, Inc., Lincolnshire, Ill.

[21] Appl. No.: 522,164

[22] Filed: May 11, 1990

[51] Int. Cl.$^5$ .............................. G01J 3/50; G01J 1/48
[52] U.S. Cl. .................................... 250/226; 356/402; 250/211 J; 250/239; 422/87
[58] Field of Search .................... 250/226, 221 J, 239; 356/402, 407; 422/58, 87, 86, 59; 436/165

[56] References Cited

U.S. PATENT DOCUMENTS

| | | |
|---|---|---|
| 4,023,930 | 5/1977 | Blunck et al. . |
| 4,115,067 | 9/1978 | Lyshkow . |
| 4,181,699 | 1/1980 | Kitzinger . |
| 4,245,997 | 1/1981 | Wiesner . |
| 4,421,719 | 12/1983 | Burleigh . |
| 4,472,353 | 9/1984 | Moore .................................. 422/87 |
| 4,617,277 | 10/1986 | Bohl . |
| 4,681,454 | 7/1987 | Breemer . |
| 4,806,491 | 2/1989 | Heim . |
| 4,906,839 | 3/1990 | Lee ....................................... 250/239 |
| 4,913,881 | 4/1990 | Evers ..................................... 422/58 |
| 4,972,089 | 11/1990 | Stevenson ........................... 250/239 |

Primary Examiner—David C. Nelms
Assistant Examiner—Michael Messinger
Attorney, Agent, or Firm—Willian Brinks Olds Hofer Gilson & Lione

[57] ABSTRACT

A monitor for the detection of a target gas by sensing the color change of a colorimetric indicator material. The monitor includes a light detector positioned and having a surface oriented to receive light reflected from the colorimetric indicator material and a light source positioned between the colorimetric indicator material and the light detector and oriented to provide illumination to the colorimetric indicator material but not to the light detector.

14 Claims, 2 Drawing Sheets

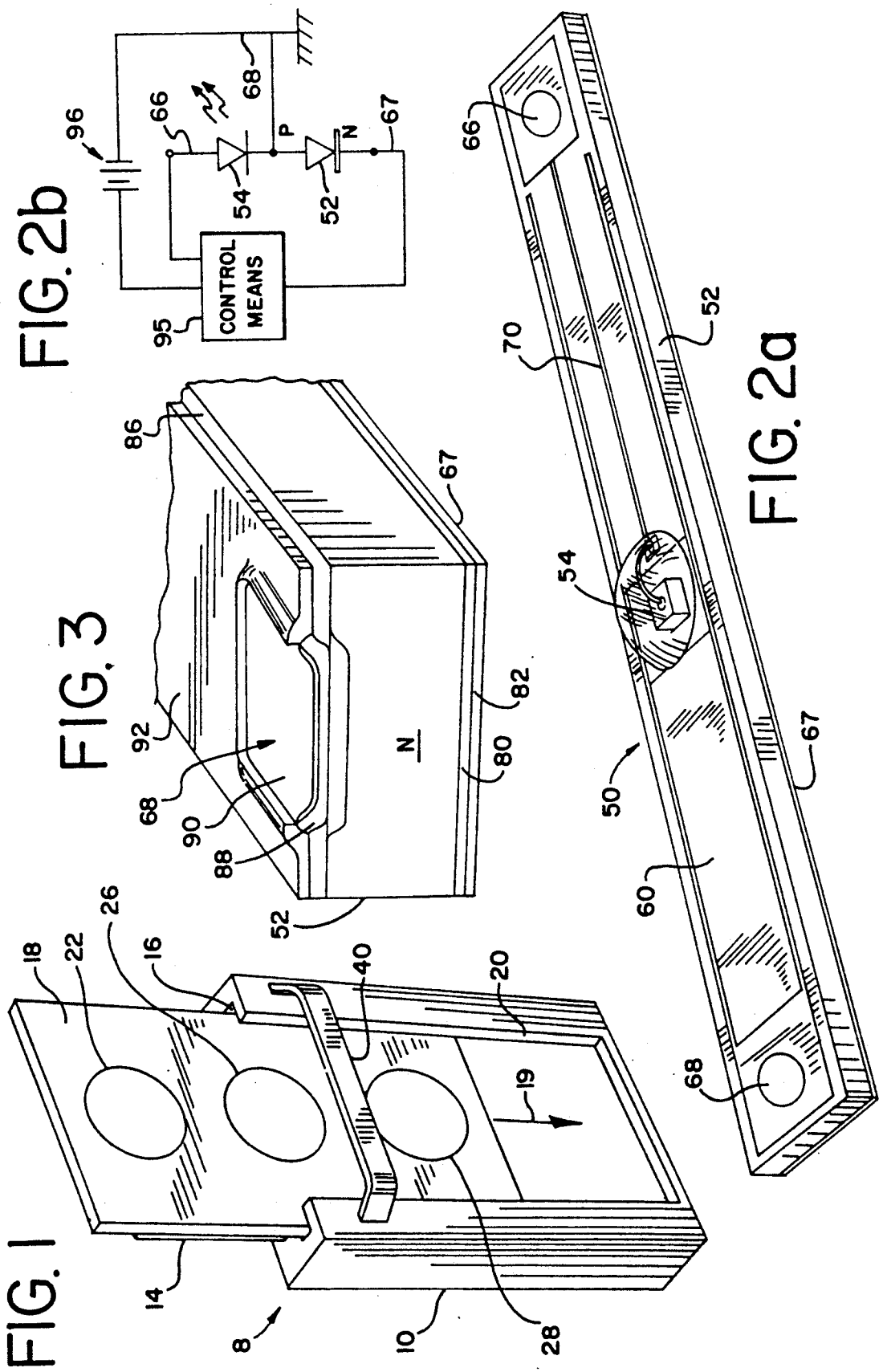

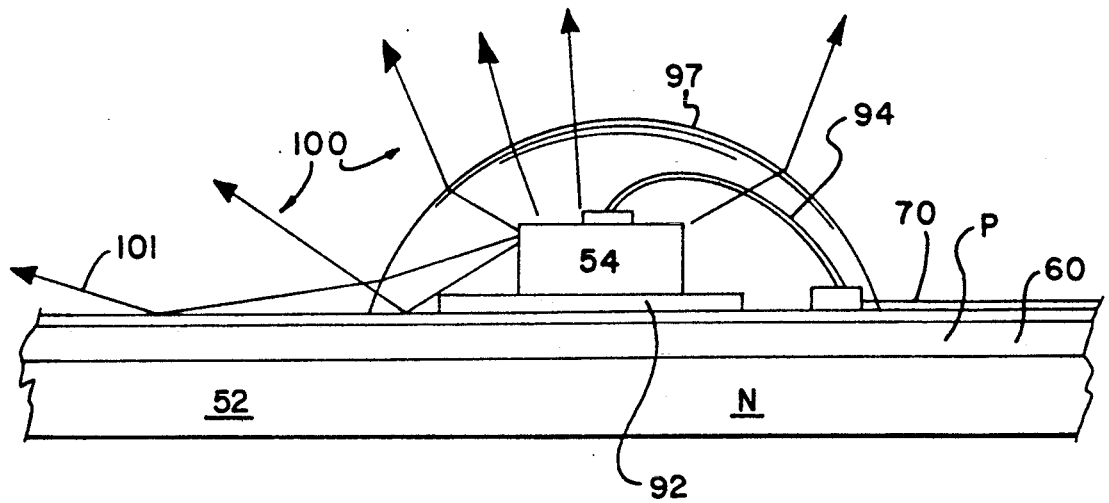
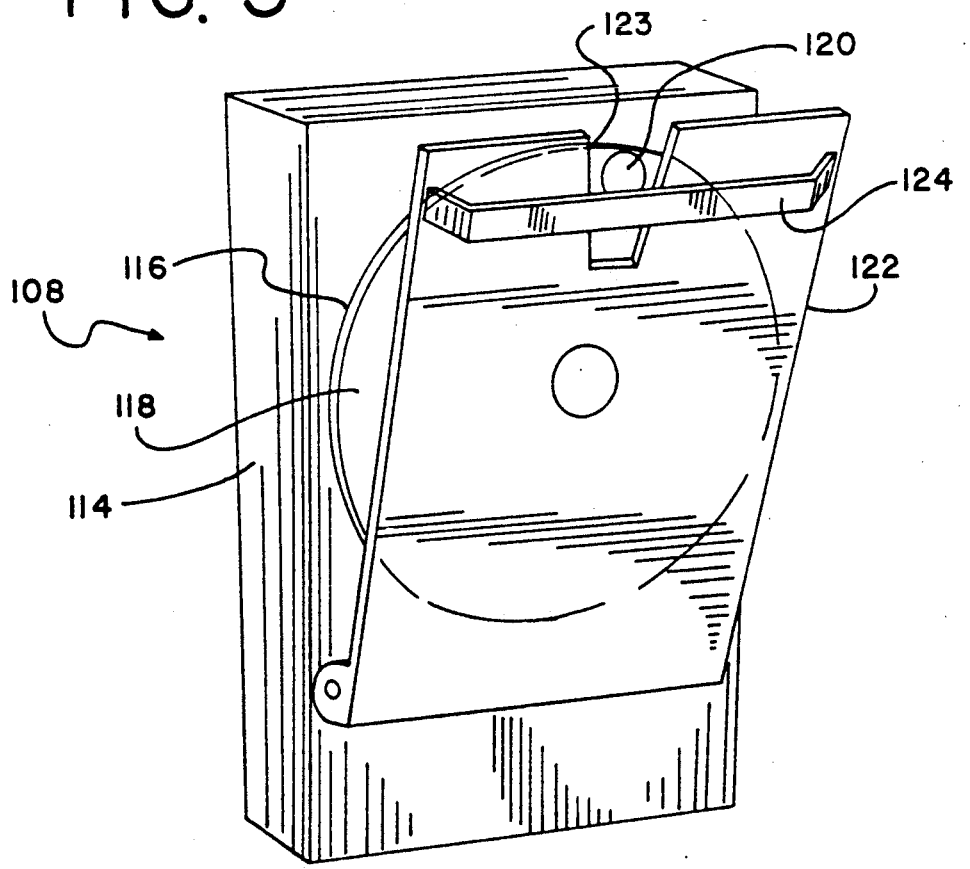

COLORIMETRIC DETECTION APPARATUS

BACKGROUND OF THE INVENTION

The present invention relates to air monitors and more particularly to air monitors of the type that may be worn or otherwise carried by an individual person (i.e. a personal air monitor) working or otherwise present in an environment where there is a hazard of exposure to certain toxic gases.

Devices have been developed that monitor the air to which a person is exposed in order to detect the presence of one or more certain hazardous gases in the environment in which the person is working. Devices of this type combine the operations of detecting a concentration of the hazardous gas that exceeds a predetermined threshold level and alerting the person about the detection of the gas. In order to perform these operations, the device must first necessarily obtain a representative sample of the air, detect the presence of one or more certain gases (i.e. target gases) in the sample rapidly, and alert the user to the detection of a concentration of the gas that exceeds a predetermined threshold level.

A well developed approach to detection of hazardous gases uses colorimetric indicators. With this approach, certain chemicals are used as indicators of a level of concentration of a particular gas. These chemicals undergo a significant color change when exposed to a particular gas. Colorimetric indicator reactions are employed in present detection devices by providing personnel who work in locations having the potential for exposure to certain target gases with badges that can hold strips of paper impregnated with a chemical colorimetrically sensitive to the specific target gas. These badges are then worn by the personnel. Such badges can be designed that are inexpensive to produce and very sensitive to the target gas.

One consideration associated with the use of a badge of this type is exposing the paper in the badge to an adequate supply of the environmental air (this combines the tasks of obtaining a sample of the air in the environment and bringing it into contact with the paper). Another consideration relates to detecting the color change in order to alert the badge wearer of such change.

Some air monitor devices are known in which a light sensor is positioned over the colorimetrically sensitive paper strip to measure the change of color of the paper. In order to eliminate or minimize the effects of extraneous or ambient light while measuring the color change of the paper, these devices have required lenses or collimators positioned over the paper. This causes the monitors to be bulky and inconvenient to wear and use. Another consideration related to positioning a sensor over the colorimetric material is that the sensor should not interfere with the exchange of air between the material and the ambient environment.

Some previous devices use a pump or other means to move the air into contact with the strip. This however also increases the size, weight, and bulk of the device and further requires the provision of a power source to operate the pump.

Accordingly, with these concerns and others taken into consideration, it is an object of the present invention to provide a gas monitor badge in which the wearer can be readily alerted to an exposure to a hazardous gas.

It is another object of the invention to provide a monitor device that can be worn readily by personnel in areas where there is potential for exposure to hazardous gas.

It is another object of the present invention to provide a monitor for the exposure to hazardous gases that minimizes power source requirements.

In addition to above concerns, a further consideration of increasing significance in the monitoring of exposure to hazardous gases in a working environment relates to monitoring of exposure duration. Standards for exposure to certain gases are in some cases considered in terms of not just a single instantaneous exposure threshold level, but rather in terms of a cumulative exposure to a level over a period of time.

Accordingly it is also an object of the present invention to provide a gas exposure monitor that measures exposure to one or more certain target gases over a period of time.

SUMMARY OF THE INVENTION

The present invention provides for a monitor for the detection of a target gas by the sensing of a color change of a colorimetric indicator material. The monitor includes a light detector positioned and having a surface oriented to receive light reflected from the colorimetric indicator material and a light source positioned between the colorimetric indicator material and the light detector and oriented to provide illumination to the colorimetric indicator material but not to the light detector.

BRIEF DESCRIPTION OF THE DRAWINGS

FIG. 1 is a perspective view of a first preferred embodiment of the present invention.

FIG. 2a is a perspective view of a light source and detector used in conjunction with the embodiment of FIG. 1.

FIG. 2b is a schematic of the embodiment depicted in FIG. 2a.

FIG. 3 is a perspective view of an end of the detector used in the embodiment depicted in FIG. 2a.

FIG. 4 is a side view of the light source used in the embodiment depicted in FIG. 2a.

FIG. 5 is a perspective view of a second preferred embodiment of the present invention.

DETAILED DESCRIPTION OF THE PRESENTLY PREFERRED EMBODIMENTS

In FIG. 1, there is depicted a first preferred embodiment of the present invention. In this first embodiment, the invention comprises a personal air monitor 8 which is of a size that can conveniently be worn by a person. In this embodiment, the monitor is approximately 4 inches high, 3 inches wide, and 0.75 inches deep.

In this first preferred embodiment, the personal air monitor 8 operates by direct exposure to ambient air in the environment (i.e., without pumping). For this reason, a monitor of this type may be referred to as a diffusion badge. A means for fastening (not shown in FIG. 1) the personal air monitor 8 to a person or a person's garment will also typically be provided. Such fastening means may comprise a clamp, hook, strap, clip, button or the like.

In this first embodiment, the personal air monitor 8 comprises a holder 10 that provides for the positioning therein of a material 14 colorimetrically sensitive to one or more certain gases to be monitored. This material 14 is typically a strip of paper impregnated with a chemical that changes color when exposed to certain gases, e.g. the target gas or gases. Gases that can be monitored by a colorimetrically sensitive material in this manner include phosgene, isocyanates, hydrogen sulfide, and hydrides, such as arsine, diborene, and phosphine. This list of gases is not intended to be complete and other gases may be detected by the colorimetric method now and in the future. The scope of the present invention is intended to include the use of any and all of these.

The strip of paper impregnated with the colorimetrically sensitive material is typically replaceable and a new strip is inserted for each work shift or at other regular intervals. The material 14 is inserted together with a shield 18 into a slot 16 of the holder 10 from the top thereof in the direction as indicated by the arrow 19. As depicted in FIG. 1, the material 14 and the shield 18 are in a position only partially inserted into the holder 10 in order to illustrate insertion of the material 14 and the shield 18; however it should be evident that during use of the personal air monitor 8, the material 14 and the shield 18 will be fully inserted into the holder 10.

The holder 10 has an open side 20 to allow ambient air to diffuse to the colorimetrically sensitive material 14 retained therein. In a preferred embodiment, the material 14 is retained in the holder 10 positioned behind a shield, such as the shield 18, having one or more openings to expose portions of the material 14 to the air. Thus, the shield 18 provides that the material 14 is exposed to the ambient air only at one or more specific locations. For this purpose, the shield 18 includes several openings 22, 26, and 28. The material 14 is directly exposed to ambient air through a first opening 22 in the shield. A second opening 26 is covered by a transparent material in order that the material is visible through the opening but completely sealed from the ambient atmosphere. The third opening 28 is covered with a material that is partially permeable to ambient air. This arrangement of these three openings provides a control indication of the level of exposure if such exposure does take place.

The personal air monitor 8 further includes a bridge 40 that is connected to the holder 10 and spans the completely exposed material 14 contained therein. The bridge 40 may be connected at either end to the holder 10 or may be connected at only one end thereof and cantilevered over it. The underside of the bridge is approximately 0.135 inches from the strip. On the side of the bridge 40 facing the material 14 is a photodetector assembly 50, depicted in FIGS. 2-4.

The photodetector assembly 50 preferably includes both a light source 54 for illumination of the colorimetric material and a detector portion 52 for detection of the color change and read out. In the preferred embodiment, the detector portion 52 is comprised of a generally elongate rectangular block of semiconductor formed to be a P-i-N photodetector. The P part of the photodetector is diffused onto one side to form an active area 60 (i.e., the area sensitive to light). This active area 60 forms part of the surface of the detector portion 52 facing the material 14. The detector portion 52 produces an electrical output signal in response to the incidence of light upon the active area 60. Design and construction of a photodetector having an active area such as described is well known in the art.

The light source 54 is located to illuminate the material 14 in the holder 10 at a location so that the detector portion 52 can sense a change in color of the material. In this embodiment, the light source 54 is located on the bridge 40 preferably on the detector portion 52 of the assembly 50 generally centrally on the active portion 60 so that on either side thereof and extending toward the ends of the assembly 50 are areas identical or approximately so in dimension of the active area portion 60 of the detector 52.

The photodetector assembly 50 includes three contacts 66, 67, and 68. One of these contacts 66 is connected to the light source 54 by means of a lead 70. The contact 67 is connected to the "N" side of the P-i-N detector which in FIG. 3 is on the bottom. The contact 68 is connected to the ground sides of the light source 54 and the P-i-N detector (the P side). In FIG. 2b, there is a schematic of the wiring connection of the light source 54 and the detector 52.

Referring to FIG. 3, there is depicted an end view in perspective of the photodetector assembly 50. The detector portion 52 is constructed of N-type material with a P-type layer diffused in one side. The N portion of the photodetector includes a contact 67 formed thereto. In order to produce a suitable contact 67 for the N side, layers 80 and 82 of chrome and gold respectively are deposited to the N side of the detector. Although chrome and gold are used in the preferred embodiment, other suitable materials may be used.

Around the area where the P-type layer is diffused onto the semiconductor, a layer of oxide 86 will typically be present. In order to form the contact 68 for the P side of the detector, a layer of aluminum 88 is deposited to a portion of the P side of the detector at an end thereof. A layer of gold 90 is then deposited to the aluminum layer 88 to form the contact 68. The surface of the detector 52 including the active area 60 is coated with a layer of glass 92, i.e. silicon monoxide.

The detailed configuration of the photodetector as disclosed herein is a preferred embodiment chosen to maximize the active area yet minimize the overall size which may slow or otherwise impede diffusion of the ambient atmosphere to the colorimetric material. It is understood that other configurations may be designed for the photodetector and it is intended the scope of this invention not be particularly limited to such details of construction as disclosed herein.

Referring to FIG. 4, there is depicted a side view of the light source 54. The light source 54 is preferably an LED (light emitting diode) having dimensions of 0.007 by 0.007 inches The light source 54 may preferably be chosen to be of a certain color, that maximizes the change in reflected light from the material 14 associated with exposure of the material to the target gas.

In other preferred embodiments, more than one light source may be included. Only certain color changes can be produced with colorimetric indicators and different color changes are associated with different indicators for different target gases. Accordingly, it is advantageous to use a light source that is exactly complementary to the color change in order to maximize the sensitivity of the signal. Moreover, it is a further advantage if the light source can be readily adjusted to produce the exact complementary color depending upon the colorimetric material used.

In one embodiment, the light source is comprised of LED's of three primary colors, e.g. red, green and blue. These LED's may be operated in combination to produce a full spectrum range of colors. Thus, the light source may be provided that illuminates with a color that is exactly complementary to the color change of the colorimetric material. This maximizes the detector's ability to sense the color change. In this manner, the detector assembly can be standardized and readily adaptable for use with various colorimetric indicators presently available as well as new indicators having different color changes that may become available in the future.

The light source 54 is mounted on a pad 92 which in turn is mounted on the detector 52. The light source 54 is connected to the contact 66 via a lead 70 that traverses the active area 60. A jumper 94 may be used to connect the light source 54 to the lead 70, if necessary. The light source 54 and the detector 52 are connected to a control means 95 such as a microprocessor via the contacts 66, 67 and 68, as indicated in FIG. 2b. The control means 95 effects operation of the light source and read out of the signal from the detector. A power source 96, such as a battery, is associated with the monitor 8 and connected to the control means 95 to provide power for the operation thereof.

The control means 95 and battery 96 may be positioned in the holder 10 of the monitor 8 but also may be positioned on the bridge 40 or even on the detector assembly 50. If positioned on the bridge, losses from the connection of the detector to the control means over wires or leads can be minimized.

In addition, a lens 97 covers the light source 54. Preferably, the lens 97 is a condenser lens that serves to concentrate light emanating from the light source 54 onto the material 14. The lens 97 may be formed of a bead of epoxy deposited on the light source 54. As so formed, the lens 97 also protects the connection of the light source 54 to the jumper 94 and the lead 70. In this embodiment, the lens 97 is approximately 0.025 inches in height and has a diameter of 0.050 inches.

In operation, the light source 54 pulses a light on the material. Pulses occur every second although other time periods may be used. The detector 52 provides an output indicative of the amount of light incident thereon. This output includes the light from the light source 54 reflected from the material 14. The control means 95 measures the output of the detector 52. This measurement is made both for the periods of time when the light source 54 is off (at which the time the amount of light is only from ambient light) and for the periods of time when the light source 54 is on (when the amount of light includes both ambient light and light from the light source 54 reflected off the material 14).

In a preferred embodiment, the signal from the detector is converted into counts (such as by a digital converter, as is well known in the art). The ambient light, i.e. the light measured by the detector portion 52 between pulses by the light source 54, is subtracted from the light measured during the pulses. This difference is the light reflected from the material. If the amount of light from the light source 54 reflected by the material 14 changes, the difference between the two signals is an indication of a color change of the material 14.

If the control means 95 measures such a decrease in the reflected light, an alarm is activated to alert of a measured change in color of the colorimetric material. The alarm may be in the form of a beeper or bell or the like to alert the person wearing the monitor of the change in color. The alarm may also be associated with a radio pager that informs personnel elsewhere of the potential gas exposure.

The present invention achieves a high signal to noise ratio by several innovative means. First, in the present invention the light source is placed in front of the detector, i.e. between the plane of the detector and the plane of the colorimetric material. By positioning the light source in front of the plane of the detector, a high percentage of the light produced by the light source can be utilized to illuminate the colorimetric material.

Secondly, the present invention provides a high signal-to-noise ratio because extraneous contributions to the detected light are eliminated or minimized. One source of extraneous light is from "leakage", i.e., light that shines directly from the light source to the detector. Referring again to FIG. 4, the light source 54 emits light rays depicted generally by the arrows 100. Ideally, the light from the light source should reflect from the colorimetric material back to detector portion in order to obtain a good reading having high sensitivity. If some of the light travels directly from the light source to the detector, i.e. "leakage", this light becomes a component of the total measured light. In prior devices, leakage light must be accounted for (e.g. substracted) in order to obtain a reading of the color change of the material. Even if a calibration is used to determine an approximate value for this leakage light, to the extent that it contributes to the total measured light, it can mask or at least reduce the sensitivity of the device to distinguish a color change of the material.

The present invention eliminates or reduces this leakage factor. First of all, the pad 92 is positioned between the light source 54 and active area 60 of the detector to block light in that direction. The pad 92 preferably also extends a distance in each direction from the light source 54 to eliminate leakage.

The present invention further reduces the leakage by the orientation of the surface of the detector 52 to the light source. The detector surface is oriented with respect to the direction of light from the light source so that light from the light source that travels directly from the light source to the detector (i.e. the leakage light) impinges the surface of the detector at an angle $\Theta$ greater than the critical angle. Accordingly, this leakage light, e.g. light beam 101, is reflected away from the detector. Although the leakage light is reflected away by the surface of the detector, the reflected light, i.e. the light that bounces off of the material 14 and is reflected back to the detector, will impinge the surface of the detector at an angle which is less than the critical angle of the surface. This reflected light will pass on through to the detector. The glass coating 92 applied to the surface of the detector contributes to the establishment of a surface having a well defined angle of incidence.

In addition to the pad and the surface orientation, leakage is further reduced by the lens 97. As shown in FIG. 4, the lens 97 is shaped to refract light in the direction toward the material 14 and away from the active area 60 of the detector.

Accordingly, in the present invention the amount of light reflected by the material from the light source can be maximized and the stray "leakage" eliminated or minimized. This results in the present invention providing a high signal-to-noise ratio and thus allowing a higher degree of sensitivity with the same components.

Referring to FIG. 5, there is shown a second preferred embodiment of the present invention. In this embodiment, the present invention comprises a STEL (short term exposure level) monitor 108. The STEL monitor 108 is adapted to monitor not only exposure to one or more certain gases that exceed an instantaneous threshold, but also to monitor exposures to target gas levels over more than one period of time. This is useful where there may be a risk associated with the accumulation of lower exposure levels. Accordingly, when such risk is of concern, monitoring exposure levels of a lower level but during more than one period of time, may be indicated.

Referring to FIG. 5, in this second preferred embodiment, the STEL monitor 108 includes a holder 114 for retaining therein a strip of colorimetrically sensitive material 116. As in the previous embodiment, a shield 118 covers the material 116 except for openings, such as opening 120. In this embodiment, the material 116 and shield 118 are circular in shape.

Also, in this embodiment, the holder 114 includes a door panel 122 on the front thereof. The door panel 122 may be hinged at the bottom and may include a latch or other means to keep it closed during use. In the door 122 is an opening 123 through which a portion of the material 116 may be exposed to ambient air through the opening 120 in the shield 118.

In this embodiment, a bridge 124 with a detector assembly thereon is mounted on the door panel 122 The bridge 124 is aligned on the door panel 122 over the opening 123 so as to monitor the change in color of the material 116 exposed through the opening 120 to the ambient air. In FIG. 5, the door panel 122 is depicted in a slightly open position in order to illustrate the function and components and it should be understood that during use the door panel will normally be closed.

The STEL monitor 108 also includes a means for rotating the strip. This rotating means may be a simple motor device located inside the holder 114 and operated by a power supply such as a battery under the control of a control means. Such rotating means, power supply, and control means are components well known in the art.

The rotating means is connected to the material 116 and the shield 118 in order to rotate them together inside the holder 114 behind the door panel 122. In a preferred embodiment, the material 116 and shield 118 are not rotated continuously, but periodically. Also, when rotated, the material 116 and the shield 118 are rotated only in increments of several degrees at a time in order to bring another opening of the shield 118 into alignment with the opening of the door panel 122. These rotational increments may be made of any size consistent with the time periods between incremental rotations and the total time that the monitor will be used. Typically, the periods would add up to an entire work shift at which time the material 116 would be removed. Because only a single portion of the material is exposed at a time, by examination of all the portions, exposure over time can be determined. In addition, the approximate time of exposure can also be determined.

Aside from the provision for a larger power source required to operate the rotating means, this second embodiment would include a light source and detector components similar to those in the first embodiment. The same or a similar detector assembly could be used.

In either of the embodiments described above, the power requirements are relatively modest because the monitor operates on diffusion of ambient air thus eliminating the necessity for a pump. The present invention also provides advantages particularly suitable for the diffusion method by reducing to a minimum dimension structural elements that might hinder diffusion of the ambient air to the colorimetrically sensitive material. Moreover, the present invention also provides the advantage that it measures the colorimetric reaction in a device that both provides a high signal to noise ratio but is not bulky or awkward to wear. This is provided in part to the photodetector assembly that advantageously combines a detector having a large detection area while simultaneously reducing the problem of leakage of light from the light source to the detector.

The present invention has been described in the context of several embodiments that operate by diffusion of the ambient air into contact with the colorimetric material, i.e. a diffusion badge. This construction provides an air monitor that is sensitive and efficient as well as relatively inexpensive to produce and easy to wear. However, the present invention may also be adapted for use in an air monitor that utilizes a pump to bring the air into contact with the colorimetric material. In such a device, the present invention could provide detection sensitivity beyond the range of existing devices given the same detector components.

Further, even though the present invention is particularly suited for use as a personal air monitor, the present invention could be adapted for use in air monitors other than those worn by a person where a colorimetric sensor having high signal to noise ratio could be employed.

It is intended that the foregoing detailed description be regarded as illustrative rather than limiting, and that it be understood that it is the following claims, including all equivalents, which are intended to define the scope of the invention.

We claim:

1. A monitor for detecting the presence of a target gas in an environment by sensing the color change of a colorimetric indicator material positioned in a holder therien and exposed to the environment, the monitor comprising:
   a light detector positioned and having a surface oriented to receive light reflected from the colorimetric indicator material; and
   a light source positioned between the colorimetric indicator material and said light detector and oriented to provide illumination to the colorimetric indicator material but not to the light detector.

2. The monitor of claim 1 in which the surface of said light detector forms an angle with the direction from said light source to said surface less than a critical angle of said surface whereby light traveling from said light source toward said detector is reflected from said light detector.

3. The monitor of claim 1 further comprising:
   a lens covering said light source said lens adapted to refract light from said light source away from said light detector.

4. The air monitor of claim 1 further comprising:
   a mounting pad impermeable to light positioned between said light source and said light detector.

5. An air monitor comprising:
   a holder for exposing to ambient air a material colorimetrically sensitive to a gas to be monitored;
   a light source positioned and oriented to illuminate a material positioned in said holder; and
   a light detector having a surface with a critical angle, said light detector surface positioned to receive light reflected from the material positioned in said holder at an angle greater than said critical angle, and further in which said light detector surface is positioned with respect to said light source so that the direction from said light source to said surface is less than said critical angle.

6. The air monitor of claim 5 further comprising:
a lens positioned over said light source adapted to condense light emanating from said light source onto a material in said holder.

7. The air monitor of claim 5 in which said light source is mounted on said light detector.

8. The air monitor of claim 7 in which said light source is mounted on said light detector between said light detector and a material retained in said holder.

9. The air monitor of claim 8 further comprising:
a mounting pad impermeable to light positioned between said light source and said detector.

10. The air monitor of claim 5 in which said light detector comprises:
a P-i-N photodetector.

11. The monitor of claim 5 in which said light source comprises:
a light emitting diode.

12. An air monitor comprising:
a holder for exposing to ambient air a strip of material colorimetrically sensitive to a gas to be monitored;
a light source positioned and oriented to illuminate a strip of material positioned in said holder;
a light detector positioned and having a surface oriented to receive light reflected from the surface of a material positioned in said holder,
a condenser lens covering said light source, said lens operable to refract light from said light source away from said light detector.

13. The monitor of claim 12 in which the surface of said light detector forms an angle greater than the critical angle with the direction of light from said light source whereby light traveling from said light source to said light detector is reflected therefrom.

14. An gas exposure monitor comprising:
a holder for exposing to ambient air a portion of a material colorimetrically sensitive to a gas to be monitored and advancing the colorimetrically sensitive material periodically so as to expose another portion of the material to ambient air;
a light source oriented to illuminate a strip of material positioned in said holder;
a light detector having a surface oriented to receive light reflected from the surface of a material positioned in said holder, the surface of said light detector forming an angle with the direction of light from said light source greater than the critical angle whereby light traveling from said light source to said light detector will be reflected.

* * * * *